(12) United States Patent  
Kim

(10) Patent No.: US 6,527,696 B1
(45) Date of Patent: Mar. 4, 2003

(54) WAVE GENERATION APPARATUS

(75) Inventor: Myung Sun Kim, Seoul (KR)

(73) Assignees: Ho Cheol Kim, Kyungki-do (KR);
MEC Co., Ltd., Kyungki-do (KR)

( * ) Notice: Subject to any disclaimer, the term of this patent is extended or adjusted under 35 U.S.C. 154(b) by 0 days.

(21) Appl. No.: 09/694,278

(22) Filed: Oct. 24, 2000

(30) Foreign Application Priority Data

Mar. 31, 2000 (KR) ........................................ 2000-16747

(51) Int. Cl.[7] ................................................. A61N 2/04
(52) U.S. Cl. ........................................................ 600/13
(58) Field of Search ........................... 600/9–15, 26–28, 600/544–545; 128/897–898

(56) References Cited

U.S. PATENT DOCUMENTS

| | | | | |
|---|---|---|---|---|
| 3,753,433 A | * | 8/1973 | Bakerich et al. ............ | 600/545 |
| 4,227,516 A | * | 10/1980 | Meland et al. ................ | 600/26 |
| 4,335,710 A | * | 6/1982 | Williamson .................. | 600/28 |
| 4,834,701 A | * | 5/1989 | Masaki ........................ | 600/28 |
| 4,846,190 A | * | 7/1989 | John ........................... | 600/544 |
| 4,902,274 A | * | 2/1990 | Gleeson, III ................. | 600/27 |
| 4,928,704 A | * | 5/1990 | Hardt .......................... | 600/545 |
| 5,036,858 A | * | 8/1991 | Carter et al. ............... | 600/27 X |
| 5,076,281 A | * | 12/1991 | Gavish ....................... | 600/28 X |
| 5,299,569 A | * | 4/1994 | Wernicke et al. ......... | 600/544 X |
| 5,306,228 A | * | 4/1994 | Rubins ........................ | 600/27 |
| 5,356,368 A | * | 10/1994 | Monroe ....................... | 600/28 |
| 5,409,445 A | * | 4/1995 | Rubins ........................ | 600/27 |
| 5,480,374 A | * | 1/1996 | Van Dick .................... | 600/26 |
| 5,527,259 A | * | 6/1996 | Grace et al. ................. | 600/14 |
| 5,546,943 A | * | 8/1996 | Gould ......................... | 128/898 |
| 5,562,597 A | * | 10/1996 | Van Dick .................... | 600/26 |
| 5,899,867 A | * | 5/1999 | Collura ....................... | 600/27 |
| 6,044,292 A | * | 3/2000 | Heyrend et al. ............ | 600/544 |
| 6,071,229 A | * | 6/2000 | Rubins ........................ | 600/27 |
| 6,129,748 A | * | 10/2000 | Kamei ........................ | 600/544 |

* cited by examiner

*Primary Examiner*—Max F. Hindenburg
*Assistant Examiner*—Joseph A. Cadugan
(74) *Attorney, Agent, or Firm*—McGuireWoods LLP

(57) ABSTRACT

An alpha wave generation apparatus has a voltage controller including a first resistor connected in parallel to an adapter jack and a battery, a converter for supplying power to a microcomputer, a first coil and a diode connected in series between the first resistor and an input terminal of the converter, a second resistor for maintaining an input voltage to the microcomputer constant in level, and a capacitor being charged with an input voltage to the converter or discharging it. The alpha wave generation apparatus generates alpha waves of 4 Hz, 8 Hz, and 10 Hz which, for example, may be used to activate cerebral cells.

7 Claims, 3 Drawing Sheets

PRIOR ART

WAVE GENERATION APPARATUS

BACKGROUND OF THE INVENTION

1. Field of the Invention

The present invention relates in general to the activation of cerebral cells using the tuning of alpha waves, and more particularly to an alpha wave generation apparatus for generating alpha waves of specific frequencies and applying them to a cerebrum remaining inactive, to stimulate it and thus activate its function, thereby improving a person's memory and studying capability.

2. Description of the Prior Art

Generally, a person's mind and body are relaxed while his brain is sunk in meditation. Also, the person's brain is made active while he concentrates his attention on something. The fact that the person's cerebrum emits brain waves of a frequency of 10±12 Hz at such an active state has already been scientifically proved.

Consequently, such an active state of the cerebrum is regarded as the most preferable state in human life, which is the main object of most moral and physical cultures. However, it is next to impossible for a person to maintain the above cerebral active state whenever desiring it. As a result, there have been proposed devices for mechanically solving such maintenance.

However, such a proposed device has encountered various problems in that it stimulates a person's sight or hearing sense to make his cerebrum active. For example, firstly, the device is adapted to stimulate the sense of sight or hearing using feeble energy. In this case, the stimulation is getting to be a cerebral habit, resulting in a reduction in effect. Secondly, the person cannot hear other ambient information when his ears are covered by the device. Thirdly, the person cannot view a book and other objects when his eyes are covered by the device.

In order to overcome the above problems, there have been studied and proposed devices wherein a coil for generation of an electromagnetic field of a specific frequency is put around a person's head to stimulate his cerebrum.

FIG. 1 is a circuit diagram showing the construction of a conventional cerebral cell activation apparatus put around a person's head, which is disclosed in Korean Patent Publication No. 96-623.

As shown in FIG. 1, the cerebral cell activation apparatus comprises a voltage controller 1 including a transformer T having primary, secondary and tertiary coils T1, T2 and T3 at a predetermined turn ratio. A transistor Q3 has its base connected to an output terminal of the primary coil T1 of the transformer T and its collector connected to an output terminal of the secondary coil T2 of the transformer T. First and second transistors Q1 and Q2 are connected in a Darlington manner through the primary coil T1 of the transformer T to drive the third transistor Q3. A first diode D1, a light emitting diode LED, resistors R1 and R2 and a first variable resistor VR1 for a potentiometer are connected to an output terminal of the tertiary coil T3 of the transformer T. The first transistor Q1 has its base connected to a variable terminal of the first variable resistor VR1 via a first Zener diode ZD1.

The cerebral cell activation apparatus further comprises an oscillator 2 including a first capacitor C1 being charged with an output voltage from the voltage controller 1 or discharging it. A second capacitor C2 and a second Zener diode ZD2 are connected in parallel to the first capacitor C1 via a resistor R4 and a second diode D2. A programmable unijunction transistor PUT has its anode connected to a resistor R5 and a second variable resistor VR2, its gate connected to a common connection point of resistors R8 and R9 and its cathode connected to a resistor R7.

The cerebral cell activation apparatus further comprises an output circuit 3 including a silicon controlled rectifier SCR having its gate connected to an output terminal of the oscillator 2. The silicon controlled rectifier SCR further has its anode connected to a common connection point of a diode D5 and a ringing coil L.

Now, a description will be given of the operation of the conventional cerebral cell activation apparatus with the above-mentioned construction.

First, when the cerebral cell activation apparatus is powered on, a voltage is applied to the collector of the third transistor Q3 via the secondary coil T2 of the transformer T and then transferred to the base of the first transistor Q1 via a fixed bias resistor R3 connected thereto. As a result, the first transistor Q1 is turned on and current flows through the primary coil T1 of the transformer T, thereby causing the second transistor Q2 to be turned on.

At this time, a sinusoidal wave signal of 8–12 KHz is generated in the secondary coil T2 of the transformer T, resulting in a counter electromotive force being induced in the tertiary coil T3 of the transformer T. As a result, the third transistor T3 is turned on, thereby causing the first capacitor C1 to be charged with a counter electromotive force triggered by the first diode D1, which has charged the first capacitor C1 with an electromotive force.

On the other hand, if a voltage across the first variable resistor VR1 for the potentiometer exceeds a threshold voltage set in the first Zener diode ZD1, then the Zener diode ZD1 conducts to turn off the first transistor Q1. Further, an electromotive force charged on the first capacitor C1 is stabilized by the second Zener diode ZD2 and second capacitor C2 via the resistor R4 and second diode D2. The programmable unijunction transistor PUT generates a saw tooth wave signal of 4–20 Hz for the trigger of the silicon controlled oscillator SCR according to a difference between a voltage set therein and a voltage dropped through the resistor R5, the second variable resistor VR2 and the resistors R8 and R9. At this time, the saw tooth wave signal is adjusted in level by adjusting a resistance of the second variable resistor VR2. Then, the triggering saw tooth wave signal generated by the programmable unijunction transistor PUT is applied to the gate of the silicon controlled rectifier SCR to turn the rectifier on, thereby changing the coil L from a ringing state to a resonant state. As a result, the first capacitor C1, which has been charged with a counter electromotive force, is recharged with an electromotive force via the diode D5.

With the operation being performed in the above manner, a signal of a desired frequency is generated in the ringing coil L and then applied to cerebral cells to stimulate them.

However, the above-mentioned conventional cerebral cell activation apparatus has a disadvantage in that it cannot generate alpha (α) waves. Further, it may rather disturb brain waves of a person because the ringing coil L is designed to oscillate at a frequency varying continuously from 1 to 20 Hz.

For these reasons, the conventional cerebral cell activation apparatus exerts partial effects on physical relaxation and sleep regulation, but has no effect on an increase in the studying efficiency of students or the working efficiency of workers.

SUMMARY OF THE INVENTION

Therefore, the present invention has been made in view of the above problems, and it is an object of the present invention to provide an alpha wave generation apparatus for generating alpha waves of 4 Hz, 8 Hz and 10 Hz capable of activating cerebral cells and applying them to a cerebrum to stimulate it and thus activate its cells, thereby improving a person's studying effect and concentration, getting rid of his stress, lending him assistance to the promotion in his health, clearing up his insomnia, improving the competitiveness of athletes and enhancing the intellectual power of children of little intelligence as much as possible.

It should be noted that the present alpha wave generation apparatus is applicable to all industrial fields desiring the alpha waves as well as the above-mentioned object.

In accordance with the present invention, the above and other objects can be accomplished by a provision of an alpha wave generation apparatus comprising voltage control means including a first resistor connected in parallel to an adapter jack and a battery, a converter for supplying power to a microcomputer, a first coil and a first diode connected in series between the first resistor and an input terminal of the converter, a second resistor for maintaining an input voltage to the microcomputer constant in level, and a first capacitor being charged with an input voltage to the converter or discharging it; function control means including an ON/OFF switch, a grade DOWN switch, a grade UP switch and a function switch; display means for providing a visual indication of the present operation state to the user; the microcomputer for controlling the entire system operation and performing an analog/digital conversion function, a pulse width modulation function and a digital/analog conversion function; frequency generation means including frequency oscillation means for performing a frequency oscillating operation in response to a control signal from the microcomputer, and reset means for resetting the system when an abnormal state occurs in the system, the reset means including a plurality of third resistors, a second capacitor and a first transistor; and output means including amplification means for amplifying an output frequency signal from the frequency generation means and outputting the amplified signal through a second coil, and analog output means for outputting a control signal to the amplification means in response to an output signal from the function control means, the analog output means including a second transistor turned on in response to a function selected by the function switch, and a transformer having a primary coil for receiving an output voltage from the voltage control means via a bias resistor when the second transistor is turned on and a secondary coil for inducing a voltage at a predetermined turn ratio relative to the primary coil, the amplification means including a third transistor for receiving the voltage induced in the secondary coil of the transformer in the analog output means via a second diode and outputting a frequency signal corresponding to the received voltage to the second coil in response to the control signal from the analog output means.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE PREFERRED EMBODIMENTS

In the case where a person concentrates his attention, his cerebral cells are activated. This advances a theory that a cerebrum can be induced to an active state by emitting an external electromagnetic field of a specific frequency to the cerebrum to stimulate its cells.

In other words, the cerebrum can be made active by compulsorily tuning it to the external electromagnetic field of the specific frequency emitted thereto and thus stimulating its cells.

On the other hand, the following results were obtained from experiments based on Lotus Brain Wave No. 1, developed by Sean Adam, a psychologist in USA. A person's cerebrum emitted beta ($\beta$) waves at 14 Hz when he was normally awake, mid alpha ($\alpha$) waves at 10 Hz when he was quick of apprehension and improved in studying capability, slow alpha ($\alpha$) waves at 8 Hz when he was increased in concentration and improved in creative faculty, and delta ($\delta$) waves at 4 Hz when he took a carefree rest, respectively.

Therefore, a main feature of the present invention is to generate frequencies of 4 Hz, 8 Hz and 10 Hz using a frequency divider differently from a prior art where a frequency is generated within the range of 1 to 20 Hz and filter the generated frequencies to accurately apply desired stimulations to cerebral cells. That is, according to the present invention, a stimulation of 4 Hz is applied to cerebral cells for a person's sleep, a stimulation of 8 Hz for person's meditation and a stimulation of 10 Hz for person's studying, respectively.

Figure 1:
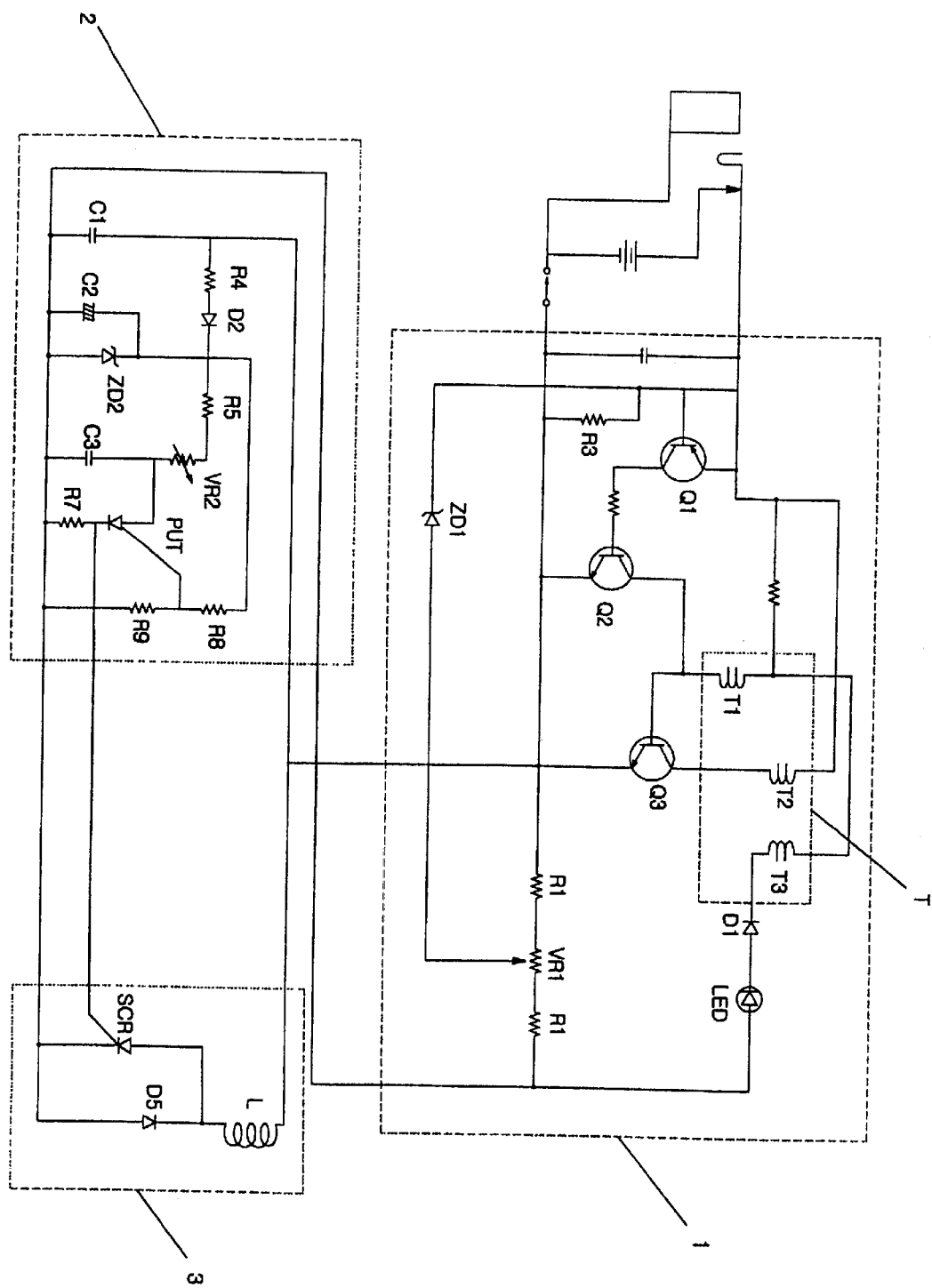
FIG. 1 is a circuit diagram showing the construction of a conventional cerebral cell activation apparatus.
Figure 2:
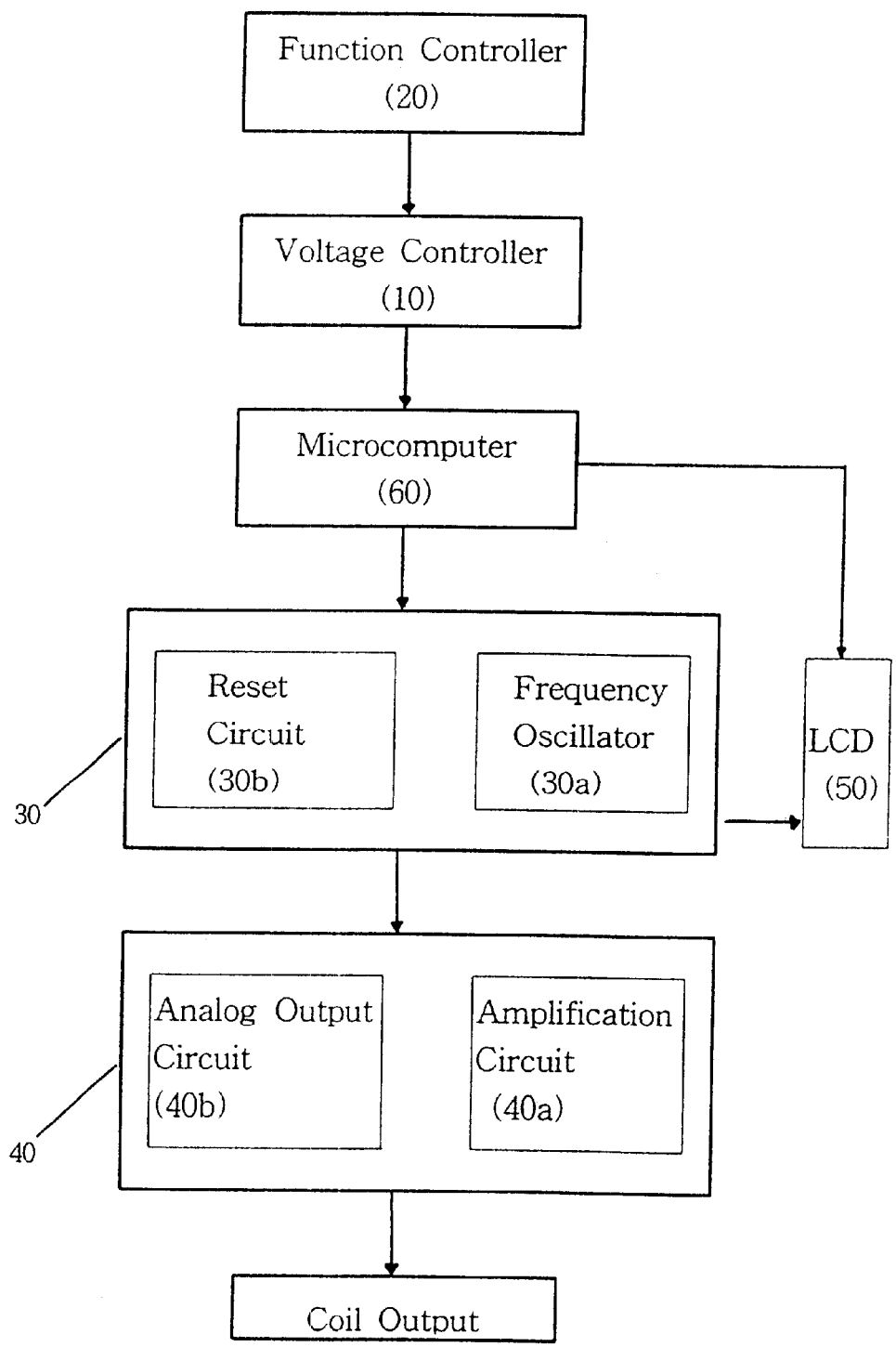
FIG. 2 is a block diagram schematically showing the construction of a cerebral cell activation apparatus in accordance with the present invention.

With reference to FIG. 2, there is schematically shown in a block form the construction of a cerebral cell activation apparatus in accordance with the present invention. In this drawing, the reference numeral 10 denotes a voltage controller for controlling the level of a voltage to a system in response to a signal inputted by the user and maintaining it constant regardless of a variation in input voltage, 20 denotes a function controller for controlling the selection of system power ON/OFF, grade DOWN/UP and other functions by the user, and 30 denotes a frequency generator for generating any one of frequencies of 4 Hz, 8 Hz and 10 Hz in response to an output signal from the function controller 20. Also, the reference numeral 40 denotes an output circuit for stimulating cerebral cells with an output frequency from the frequency generator 30, 50 denotes a liquid crystal display (LCD) for providing a visual indication of the present frequency to the user, and 60 denotes a microcomputer for controlling the entire system operation and performing an analog/digital conversion function, a pulse width modulation function and a digital/analog conversion function.

Figure 3:
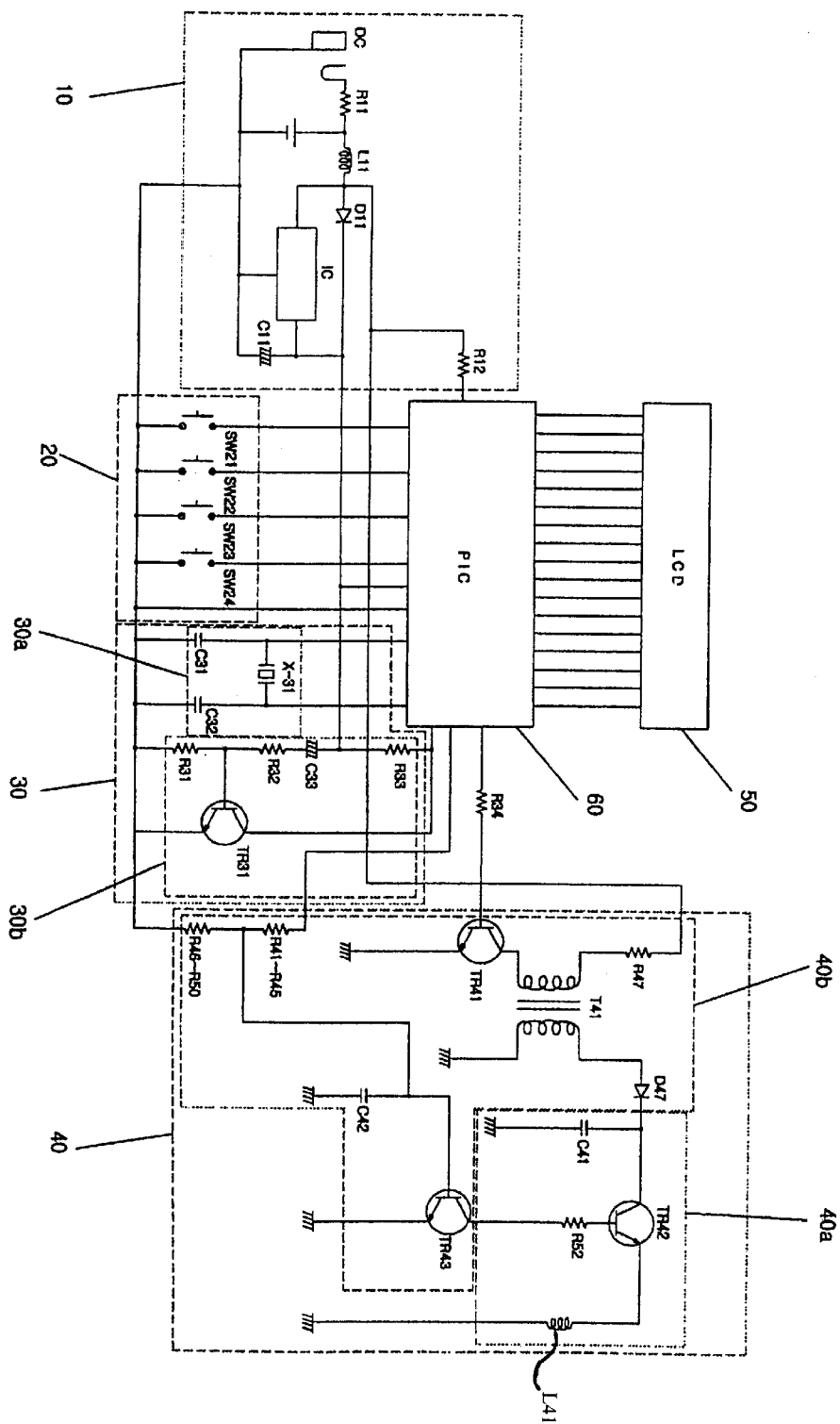
FIG. 3 is a circuit diagram in detail showing the construction of the cerebral cell activation apparatus in accordance with the preferred embodiment of the present invention.

In more detail, as shown in FIG. 3, the voltage controller 10 includes a resistor R11 connected in parallel to an adapter jack and a battery, a converter 10a for supplying power to the microcomputer 60, a coil L11 and a diode D11 connected in series between the resistor R11 and an input terminal of the converter 10a, a resistor R12 for maintaining an input voltage to the microcomputer 60 constant in level, and a capacitor C11 being charged with an input voltage to the converter 10a or discharging it.

The function controller 20 includes an ON/OFF switch SW21, a grade DOWN switch SW22, a grade UP switch SW23 and a function switch SW24.

The frequency generator 30 includes a frequency oscillator 30a, and a reset circuit 30b for resetting the system when an abnormal state occurs in the system. The frequency oscillator 30a is provided with a crystal X-31 for performing a frequency oscillating operation, and a pair of capacitors C31 and C32 for coupling the crystal X-31. The reset circuit 30b is provided with a plurality of resistors R33, R31 and R32, a capacitor C33 and a transistor TR31.

The output circuit 40 includes an amplification circuit 40a for amplifying an output frequency signal from the frequency generator 10 and outputting the amplified signal through a coil L41, and an analog output circuit 40b for outputting a control signal to the amplification circuit 40a in response to an output signal from the function controller 20. The analog output circuit 40b includes a switching transistor TR41 turned on in response to a function selected by the function switch SW24, a transformer T41 having a primary coil for receiving an output voltage from the voltage controller 10 via a bias resistor R51 when the switching transistor TR41 is turned on and a secondary coil for inducing a voltage at a predetermined turn ratio relative to the primary coil, a plurality of resistors R41–R50 for performing a voltage dividing function in response to a grade mode selected by the grade DOWN and UP switches SW22 and SW23, a bypass capacitor C42 for bypassing an output voltage from the resistors R41–R50, and a control transistor TR43 for outputting the control signal to the amplification circuit 40a in response to an output voltage from the bypass capacitor C42. The amplification circuit 40a includes an output transistor TR42 for receiving the voltage induced in the secondary coil of the transformer T41 in the analog output circuit 40b via a diode D41 and outputting a frequency signal corresponding to the received voltage to an external headband or earphone (not shown) via the coil L41 in response to the control signal from the control transistor TR43 in the analog output circuit 40b.

Next, a detailed description will be given of the operation of the cerebral cell activation apparatus with the above-mentioned construction in accordance with the present invention.

First, if the user powers on the system using the ON/OFF switch SW21 in the function controller 20, then a voltage of 1.2V from the battery is supplied to the converter 10a through the resistor R11, coil L11 and diode D11, thereby causing the converter 10a to output a constant voltage of 5V to the microcomputer 60 regardless of a variation in input voltage so that the microcomputer 60 can stably be operated.

The grade switches SW22 and SW23 are adapted to select any one of grade modes, or an elementary grade mode, an intermediate grade mode and a high grade mode, under the control of the user. The elementary grade mode signifies that the user uses the present apparatus for the first time, the intermediate grade mode signifies that the user has used the present apparatus several times, and the high grade mode signifies that the user is a person of a well-cultivated mind such as a Buddhist monk. The function switch SW24 is adapted to select any one of studying, sleep and meditation functions under the control of the user. For example, in the case where the grade switches SW22 and SW23 select the elementary grade and the function switch SW24 selects the sleep function, the microcomputer 60 displays the elementary grade mode and sleep function selected by those switches on the LCD 50.

If the elementary grade mode and sleep function are selected in the above manner, then the microcomputer 60 generates a control signal for the generation of a frequency of 4 Hz and applies the generated control signal to the crystal X-31 in the frequency oscillator 30a. As stated previously, according to the present invention, a stimulation of 4 Hz is applied to cerebral cells for a person's sleep, a stimulation of 8 Hz for person's meditation and a stimulation of 10 Hz for person's studying, respectively.

In response to the control signal from the microcomputer 60, the crystal X-31 generates the frequency of 4 Hz and transfers it to the output circuit 40.

Provided that the microcomputer 60 outputs no control signal corresponding to the mode and function selected by the respective switches in the function controller 20, the reset circuit 30b resets the system to resume the output of a frequency corresponding to the selected mode and function.

In the output circuit 40, the switching transistor TR41 is turned on in response to the output frequency from the frequency generator 30 to transfer the output voltage from the voltage controller 10 to the primary coil of the transformer T41 via the bias resistor R51. Subsequently, a voltage is induced in the secondary coil of the transformer T41 according to a predetermined turn ratio relative to the primary coil of the transformer T41 and then transferred to the amplification circuit 40a. The amplification circuit 40a outputs a frequency signal corresponding to the received voltage to an external auxiliary device via the coil L41 to make cerebral cells active.

The analog output circuit 40b generates a voltage corresponding to a grade mode selected according to whether the user is an unskilled person or a skilled person and applies the generated voltage to the base of the output transistor TR42 to turn on the transistor TR42. Namely, the voltage corresponding to the selected grade mode is applied to the base of the control transistor TR43 via the resistors R41–R50 and bypass capacitor C42 to turn on the transistor TR43. As the transistor TR43 is turned on, the output transistor TR42 is turned on to transfer the frequency signal to the coil L41.

At this time, the battery power is consumed about 70% of its entire amount at most due to charging and discharging operations of the capacitor C11 based on an electromotive force and a counter electromotive force via the diode D11. This has the effect of reducing power consumption of the battery. Further, the microcomputer is operated at a low voltage to convert an analog signal into a digital signal and control the output voltage using the digital signal. As a result, the output voltage is raised in level, but current associated therewith is significantly reduced in amount, resulting in no harm to the human body.

As apparent from the above description, the present invention provides an alpha wave generation apparatus which generates alpha waves of 4 Hz, 8 Hz and 10 Hz capable of activating cerebral cells and applies them to a cerebrum to stimulate it and thus activate its cells. Therefore, the alpha wave generation apparatus can improve a person's studying effect and concentration, get rid of his stress, lend him assistance to the promotion in his health and clear up his insomnia. Further, the present apparatus can improve the competitiveness of athletes and enhance the intellectual power of children of little intelligence as much as possible.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A wave generation apparatus comprising:

voltage control means including:
- a first resistor connected in parallel to an adapter jack and a battery,
- a converter for supplying power to a microcomputer,
- a first coil and a first diode connected in series between said first resistor and an input terminal of said converter,
- a second resistor for maintaining an input voltage to said microcomputer constant in level, and
- a first capacitor being charged with an input voltage to said converter or discharging it;

function control means including an ON/OFF switch, a grade DOWN switch, a grade UP switch and a function switch, the function control means including a function controller circuit including a switch for allowing a user to select one of a plurality of frequencies to cause a particular cerebrum response, said plurality of frequencies comprising 4 Hz for inducing a rest, 8 Hz for increasing concentration, and 10 Hz for improving a studying capability;

a voltage controller circuit for selecting an input voltage in response to said switch;

a frequency oscillator connected to said microcomputer for generating said selected frequency corresponding to said switch;

display means for providing a visual indication of the present operation state to the user;

a microcomputer connected to said function controller circuit and said voltage controller circuit, said microcomputer for controlling said wave generation apparatus and performing an analog/digital conversion function, a pulse width modulation function and a digital/analog conversion function;

frequency generation means including:
- frequency oscillation means for performing a frequency oscillating operation in response to a control signal from said microcomputer, and
- reset means for resetting the system when an abnormal state occurs in the system, said reset means including a plurality of third resistors, a second capacitor and a first transistor; and output means including:
- amplification means for amplifying an output frequency signal from said frequency generation means and outputting the amplified signal through a second coil, and
- analog output means for outputting a control signal to said amplification means in response to an output signal from said function control means, said analog output means including:
  - a second transistor turned on in response to a function selected by said function switch, and
  - a transformer having a primary coil for receiving an output voltage from said voltage control means via a bias resistor when said second transistor is turned on and a secondary coil for inducing a voltage at a predetermined turn ratio relative to said primary coil,
  - said amplification means including a third transistor for receiving the voltage induced in said secondary coil of said transformer in said analog output means via a second diode and outputting a frequency signal corresponding to the received voltage to said second coil in response to said control signal from said analog output means.

2. The wave generation apparatus as set forth in claim 1, wherein said frequency oscillation means includes a crystal and a pair of coupling capacitors.

3. The wave generation apparatus as set forth in claim 1, wherein said analog output means includes:
- a plurality of fourth resistors for dividing an output voltage from said microcomputer at a predetermined ratio;
- a bypass capacitor for bypassing the voltage divided by said fourth resistors; and
- a fourth transistor turned on in response to an output voltage from said bypass capacitor to turn on said third transistor in said amplification means.

4. The wave generation apparatus as set forth in claim 3, wherein said fourth resistors are adapted to perform a voltage dividing function in response to a grade mode selected by said grade DOWN and UP switches.

5. The wave generation apparatus as set forth in claim 1, wherein any one of said amplification means and analog output means in said output means is adapted to provide an output frequency in response to an output signal from said microcomputer.

6. The wave generation apparatus as recited in claim 1, further comprising an amplification circuit for amplifying said individual frequencies.

7. The wave generation apparatus as recited in claim 1, further comprising a display connected to said microcomputer for displaying said selected frequency generated by said frequency oscillator.

* * * * *